(12) United States Patent
Langlois et al.

(10) Patent No.: US 6,583,319 B1
(45) Date of Patent: Jun. 24, 2003

(54) CYCLIC COMPOUNDS HAVING A CYCLOALKYLENE CHAIN

(75) Inventors: Michel Langlois, Sceaux (FR); Monique Mathe-Allainmat, Massy (FR); Marie Lefas-Le Gall, Deuil la Barre (FR); Caroline Bennejean, Charenton le Pont (FR); Pierre Renard, Le Chesnay (FR); Philippe Delagrange, Issy les Moulineaux (FR)

(73) Assignee: Les Laboratoires Servier, Neuilly-sur-Seine (FR)

( * ) Notice: Subject to any disclaimer, the term of this patent is extended or adjusted under 35 U.S.C. 154(b) by 0 days.

(21) Appl. No.: 09/415,648

(22) Filed: Oct. 12, 1999

(30) Foreign Application Priority Data

Oct. 12, 1998 (FR) .............................. 98 12738

(51) Int. Cl.$^7$ .................. C07C 233/23; A01N 37/18
(52) U.S. Cl. .................. 564/180; 564/215; 564/219; 514/622; 514/630
(58) Field of Search ................ 564/215, 219, 564/180; 514/622, 630

(56) References Cited

U.S. PATENT DOCUMENTS 5,236,953 A * 8/1993 Hughes et al. .............. 514/522
5,668,180 A * 9/1997 Lesieur et al. .............. 514/630
5,731,352 A * 3/1998 Lesieur et al. .............. 514/630
5,780,512 A * 7/1998 Lesieur et al. .............. 514/624

OTHER PUBLICATIONS

Database CAPLUS on STN, Acc. No. 1997:53826, Lesieur et al., Preparation of N–[omega–(1–naphthyl)alkyl]alkanamides and analogs as melatoninergic agents. EP 745586 (abstract).*

* cited by examiner

*Primary Examiner*—Brian Davis
(74) *Attorney, Agent, or Firm*—The Firm of Hueschen and Sage

(57) ABSTRACT

The invention relates to compounds of for a (I):

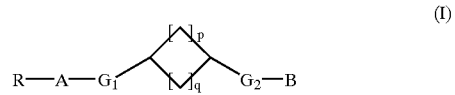

wherein:
R represents $OR_a$, $SR_a$ or $R_a$ or a cyclic group
A is a cyclic structure
$G_1$ and $G_2$ represent an alkylene chain or a single bond
B represents $-NR^1{}_aC(Q)R^2{}_a$, $-NR^1{}_aC(Q)NR^2{}_aR^3{}_a$ or $C(Q)NR^1{}_aR^2{}_a$
p and q are such that $1 \leq p+q \leq 4$,
and medicinal products containing the same which are useful in treating or in preventing melatoninergic disorders.

20 Claims, No Drawings

CYCLIC COMPOUNDS HAVING A CYCLOALKYLENE CHAIN

FIELD OF THE INVENTION

The present invention relates to new cyclic compounds having a cycloalkylene chain.

DESCRIPTION OF THE PRIOR ART

Hydroxy or alkoxy cyclopropane amides (WO 9209566, EP 436199, U.S. Pat. No. 5,459,150) and hydroxy or alkoxy cyclobutane amides (U.S. Pat. No. 5,187,192) are known from the prior art for use as 5-lipoxygenase inhibitors.

Other cyclopropane-amide or -thioamide compounds having an unsaturated chain are described as pesticides (EP 369762).

Cyclopropane-indole compounds for use in the treatment of neurodegenerative disorders (EP 568136) are also found.

Finally, some publications mention amide compounds having a cyclohexane chain as intermediates or synthesis products (Indian J. Chem., 1974, 12(7), pp. 664–7; Bull. Chem. Soc. Jap., 1968, 41(12), pp. 3008–11).

BACKGROUND OF THE INVENTION

The compounds of the present invention are new and exhibit pharmacological characteristics that are very valuable in respect of melatoninergic receptors.

Numerous studies in the last ten years have demonstrated the key role of melatonin (N-acetyl-5-methoxytryptamine) in many physiopathological phenomena and in the control of the circadian rhythm. Its half-life is quite short, however, owing to the fact that it is rapidly metabolised. Great interest therefore lies in the possibility of providing the clinician with melatonin analogues that are metabolically more stable, have an agonist or antagonist character and may be expected to have a therapeutic effect that is superior to that of the hormone itself.

In addition to their beneficial action on circadian rhythm disorders (J. Neurosurg. 1985, 63, pp. 321–341) and sleep disorders (Psychopharmacology, 1990, 100, pp. 222–226), ligands of the melatoninergic system have valuable pharmacological properties in respect of the central nervous system, especially anxiolytic and antipsychotic properties (Neuropharmacology of Pineal Secretions, 1990, 8 (3–4), pp. 264–272) and analgesic properties (Pharmacopsychiat., 1987, 20, pp. 222–223), as well as for the treatment of Parkinson's disease (J. Neurosurg. 1985, 63, pp. 321–341) and Alzheimer's disease (Brain Research, 1990, 528, pp. 170–174). Those compounds have also demonstrated activity in relation to certain cancers (Melatonin—Clinical Perspectives, Oxford University Press, 1988, pp. 164–165), ovulation (Science 1987, 227, pp. 714–720), diabetes (Clinical Endocrinology, 1986, 24, pp. 359–364), and in the treatment of obesity (International Journal of Eating Disorders, 1996, 20 (4), pp. 443–446). Those various effects are exerted via the intermediary of specific melatonin receptors. Molecular biology studies have demonstrated the existence of a number of receptor sub-types that are capable of binding that hormone (Trends Pharmacol. Sci., 1995, 16, p. 50 WO 97.04094). It has been possible, for various species, including mammals, for some of those receptors to be located and characterised. In order to be able to understand the physiological functions of those receptors better, it is of great advantage to have available specific ligands. Moreover, such compounds, by interacting selectively with one or other of those receptors, may be excellent medicaments for the clinician in the treatment of pathologies associated with the melatoninergic system, some of which have been mentioned above.

The compounds of the present invention, in addition to being new, exhibit a very strong affinity for melatonin receptors and/or selectivity for one or other of the melatoninergic receptor sub-types.

DETAILED DESCRIPTION OF THE INVENTION

The present invention relates more especially to compounds of formula (I):

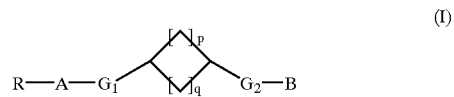

wherein
❖ A represents:
➤ a ring system of formula (II):

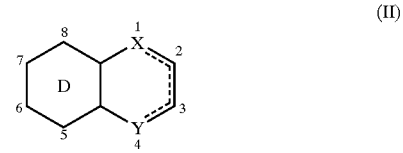

wherein X and Y, which may be identical or different, represent an oxygen atom, a sulphur atom or a $CH_2$ group,
D represents a benzene ring or a naphthalene,
and the symbol ------- means that the bonds may be single or double, with the proviso that the valency of the atoms is respected,
wherein R substitutes either the ring system D or the ring containing X and Y, and $G_1$ substitutes the ring containing X and Y,
➤ or or a ring system of formula (III):

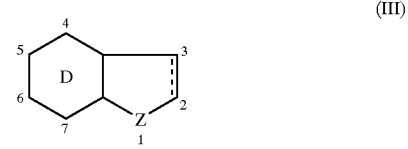

wherein Z represents an oxygen atom, a sulphur atom, a $CH_2$ group or an $NR^1$ group (wherein $R^1$ represents a hydrogen atom, a linear or branched ($C_1$–$C_6$)alkyl group, an aryl group or an aryl-($C_1$–$C_6$)alkyl group in which the alkyl moiety is linear or branched),
D' represents a benzene ring or a pyridine ring, and the symbol ------- is as defined hereinabove,
wherein R substitutes the D' ring and $G_1$ substitutes the other ring, it being understood that the ring systems of formula (II) or (III) may be substituted, in addition to the R and $G_1$ groups, by from one to three identical or different groups selected from $R_a$, $OR_a$, hydroxyl, $COR_a$, formyl, $COOR_a$, carboxyl and $OCOR_a$,
wherein $R_a$ represents a substituted or unsubstituted linear or branched ($C_1$–$C_6$)alkyl group, a substituted or unsubstituted linear or branched ($C_2$–$C_6$)alkenyl group, a substituted or unsubstituted linear or branched $(C_2-C_6)$alkynyl group, a linear or branched polyhalo-$(C_1-C_6)$alkyl group, a substituted or unsubstituted $(C_3-C_8)$cycloalkyl group, a substituted or unsubstituted $(C_3-C_8)$cycloalkyl-$(C_1-C_6)$alkyl group in which the alkyl moiety is linear or branched, a substituted or unsubstituted $(C_3-C_8)$cycloalkenyl group, a substituted or unsubstituted $(C_3-C_8)$cycloalkenyl-$(C_1-C_6)$alkyl group in which the alkyl moiety is linear or branched, an aryl group, an aryl-$(C_1-C_6)$alkyl group in which the alkyl moiety is linear or branched, a heteroaryl group or a heteroaryl-$(C_1-C_6)$alkyl group in which the alkyl moiety is linear or branched, ❖R represents a hydrogen or halogen atom, or a hydroxyl, SH, $R_a$, $OR_a$ or $S(O)_nR_a$ group wherein n is 0, 1 or 2 and $R_a$ is as defined hereinabove,
or forms, with the carbon atom carrying it and with an adjacent carbon atom, a ring of formula (IV):

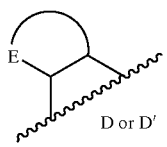

(IV)

wherein E represents an oxygen atom or an —$S(O)_n$— group wherein n is as defined hereinabove,
wherein the resulting ring contains from 5 to 7 atoms, may contain one or more unsaturations and may be substituted by one or more groups selected from linear or branched $(C_1-C_6)$alkyl, linear or branched $(C_1-C_6)$alkoxy, carboxy, linear or branched $(C_1-C_6)$alkoxycarbonyl, hydroxy and oxo, ❖$G_1$ and $G_2$, which may be identical or different, represent a single bond or an alkylene chain —$(CH_2)_t$— (wherein t is 1, 2, 3 or 4), unsubstituted or substituted by one or more identical or different radicals selected from hydroxy, carboxy, formyl, $R_a$, $OR_a$, $COOR_a$, $COR_a$, (wherein $R_a$ is as defined hereinabove) and halogen atoms, ❖p is 0,1, 2, 3 or 4,
q is 0,1, 2, 3 or 4,
with $1 \geq p+q \geq 4$, ❖B represents an —$NR^1_aC(Q)R^2_a$, —$NR^1_aC(Q)NR^2_aR^3_a$ or —$C(Q)NR^1_aR^2_a$ group wherein $R^1_a$, $R^2_a$ and $R^3_a$, which may be identical or different, can have any of the values of $R_a$ or may represent a hydrogen atom, and Q represents an oxygen or sulphur atom,
it being understood that:
the term "substituted" applied to the terms "alkyl", "alkenyl" and "alkynyl" means that those groups are substituted by one or more identical or different radicals selected from hydroxy, linear or branched $(C_1-C_6)$ alkoxy, linear or branched $(C_1-C_6)$alkyl, linear or branched polyhalo-$(C_1-C_6)$alkyl, amino and halogen atoms,
the term "substituted" applied to the terms "cycloalkyl", "cycloalkylalkyl", "cycloalkenyl" and "cycloalkenylalkyl" means that the cyclic moiety of those groups is substituted by one or more identical or different radicals selected from hydroxy, linear or branched $(C_1-C_6)$ alkoxy, linear or branched $(C_1-C_6)$alkyl, linear or branched polyhalo-$(C_1-C_6)$alkyl, amino and halogen atoms, "aryl" is understood to mean the groups phenyl, naphthyl or biphenyl, it being possible for those groups to be substituted by one or more identical or different radicals selected from hydroxy, linear or branched $(C_1-C_6)$ alkoxy, linear or branched $(C_1-C_6)$alkyl, linear or branched polyhalo-$(C_1-C_6)$alkyl, cyano, carboxy, linear or branched $(C_1-C_6)$alkoxy carbonyl, nitro, amino and halogen atoms, "heteroaryl" is understood to mean any mono- or polycyclic aromatic group containing from 5 to 10 atoms and containing from 1 to 3 hetero atoms selected from nitrogen, oxygen and sulphur, it being possible for those groups to be substituted by one or more identical or different radicals selected from hydroxy, linear or branched $(C_1-C_6)$alkoxy, linear or branched $(C_1-C_6)$ alkyl, linear or branched polyhalo-$(C_1-C_6)$alkyl, cyano, carboxy, linear or branched $(C_1-C_6)$alkoxycarbonyl, nitro, amino and halogen atoms, with the proviso that:
when A represents a naphthalene group unsubstituted or substituted by one methoxy or one methyl group, $G_1$ and G2 simultaneously represent a single bond, and B represents an

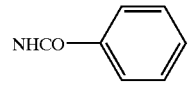

or NHCOMe group, it is not possible to have (q=0 and p=4) or (q=4 and p=0),
when $G_1$ represents a single bond and p+q=1, A cannot represent a naphthalene group substituted by one or more halogen atoms,
when A represents an indole group substituted in the 2-position by the group

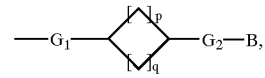

B cannot represent a urea group,
when A represents an indole group substituted in the 2-position by a carboxyl or alkoxycarbonyl group, p is 1 and q is 0 (or q is 1 and p is 0), and $G_1$ represents a single bond, B cannot represent a CONHAr group wherein Ar represents an aryl group,
their enantiomers and diastereoisomers, and addition salts thereof with a pharmaceutically acceptable acid or base.

Among the pharmaceutically acceptable acids there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, oxalic acid, etc.

Among the pharmaceutically acceptable bases there may be mentioned by way of non-limiting example sodium hydroxide, potassium hydroxide, triethylamine, tert-butylamine, etc.

The preferred compounds of the invention are those wherein p+q=1.

The preferred R substituents are the groups $R_a$, $OR_a$ and $SR_a$, more especially $R_a$ and $OR_a$ wherein $R_a$ more preferably represents a linear or branched $(C_1-C_6)$alkyl group, a $(C_3-C_8)$cycloalkyl group, a $(C_3-C_8)$cycloalkyl-$(C_1-C_6)$ alkyl group in which the alkyl moiety is linear or branched, an aryl group or an aryl-($C_1$–$C_6$)alkyl group in which the alkyl moiety is linear or branched, such as, for example, methyl, ethyl, propyl, isopropyl, butyl, sec-butyl, tert-butyl, pentyl, hexyl, cyclopropyl, cyclobutyl, cyclopentyl, cyclohexyl, cyclopropylmethyl, cyclopropylethyl, phenyl or benzyl, or those wherein R forms with the carbon atom carrying it and with an adjacent carbon atom a ring of formula (IV) wherein E represents, for example,

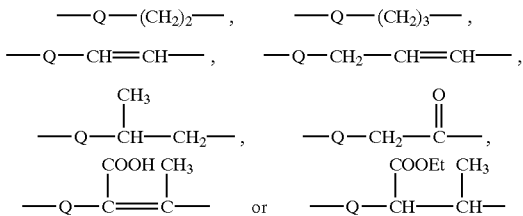

wherein Q represents a sulphur or oxygen atom.

The invention relates more preferably to compounds wherein R represents an $OR_a$ group.

More advantageously, the invention relates to compounds wherein A represents a ring system of formula (II) substituted in the 7-position by R and in the 1- or 2-position by $G_1$, or a system of formula (III) substituted in the 5-position by R and in the 3-position by $G_1$, A preferably being unsubstituted or substituted (as well as by the substituents R and $G_1$) by a group in the 2- or 3-position (formula II) or in the 2-position (formula III), this group being most preferably an alkoxy group, an aryl group or an arylalkyl group.

The preferred $G_1$ and $G_2$ groups are the single bond or the $CH_2$ group.

The invention relates more especially to compounds wherein B represents an —$NHCOR_a$ or —$CONHR_a$ group.

More advantageously, the invention relates to compounds wherein A is substituted by a group of formula (V):

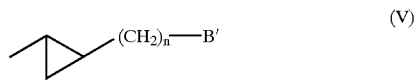

wherein n is 0 or 1 and B' represents an —$NHCOR_a$ or —$CONHR_a$ group (wherein $R_a$, is as defined hereinabove), by an alkoxy, alkylthio or alkyl group, and optionally by an alkoxy, aryl or arylalkyl group.

Still more especially, the invention relates to:

naphthalene, chroman or benzochroman compounds substituted in the 1- or 2-position (formula 11) by a group of formula (V), in the 7-position (formula 11) by an $R_a$, $OR_a$ or $SR_a$ group, and optionally substituted in the 3-position (formula II) by an aryl or arylalkyl group or in the 2-position (formula II) by an alkoxy group, or benzothiophene, benzofuran, indole or azaindole compounds substituted in the 3-position (formula III) by a group of formnula (V), in the 5-position (formula III) by an $R_a$, $OR_a$ or $SR_a$ group and optionally substituted in the 2-position (formula III) by an aryl or arylalkyl group.

Very advantageously, the invention relates to naphthalene compounds substituted in the 1-position by a group of formula (V), in the 7-position by an $OR_a$ group and optionally substituted in the 2-position by an $OR_a$ group or in the 3-position by an aryl or arylalkyl group.

The invention relates more especially to compounds of formula (I) which are

◆ N-[2-(7-methoxy-1-naphthyl)-1-cyclopropyl]acetamide
◆ N-[2-(7-methoxy-1-naphthyl)-1-cyclopropyl] propanamide
◆ N-[2-(7-methoxy-1-naphthyl)-1-cyclopropyl] butanamide
◆ N-[2-(7-methoxy-1-naphthyl)-1-cyclopropyl] cyclopropanecarboxamide
◆ N-[2-(2,7-dimethoxy-1-naphthyl)-1-cyclopropyl] acetamide
◆ N-[2-(2,7-dimethoxy-1-naphthyl)-1-cyclopropyl] propanamide
◆ N-[2-(2,7-dimethoxy-1-naphthyl)-1-cyclopropyl] butanamide
◆ N-[2-(2-methoxy-1-naphthyl)-1-cyclopropyl]acetamide
◆ N-[2-(2-methoxy-1-naphthyl)-1-cyclopropyl] acetanamide
◆ N-[2-(2-methoxy-1-naphthyl)-1-cyclopropylmethy] acetamide
◆ N-[2-(2-methoxy-1-naphthyl)-1-cyclopropylmethyl] propanamide
◆ N-[2-(2-methoxy-1-naphthyl)-1-cyclopropylmethyl] butanamide.

The preferred configuration of compounds of formula (I) is when —$G_1$—A—R group and —$G_2$—B— group are in the trans configuration.

The enantiomers, diastereoisomers and addition salts with a pharmaceutically acceptable acid or base of the preferred compounds of the invention are an integral part of the invention.

The invention relates also to a process for the preparation of compounds of formula (I) characterised in that there is used as starting material a compound of formula (VI):

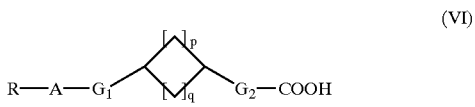

wherein R, A, $G_1$, $G_2$, p and q are as defined hereinabove,

◆ which is subjected, after activation to the acid chloride or in the presence of a coupling agent, to the action of an amine $HNR^1_aR^2a$, wherein $R^1_a$ and $R^2_a$ are as defined hereinabove to yield a compound of formula (I/a), a particular case of the compounds of formula (I):

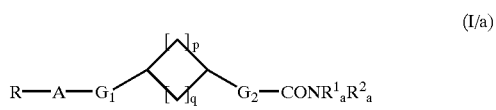

wherein R, A, $G_1$, $G_2$, $R^1_a$, $R^2_a$, p and q are as defined hereinabove, which may be subjected to the action of a thionisation agent, such as Lawesson's reagent, to obtain a compound of formula (I/b), a particular case of the compounds of formula (I),

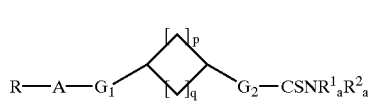 (I/b)

wherein R, A, $G_1$, $G_2$, $R^1_a$, $R^2_a$, p and q are as defined hereinabove, ❖ or subjected, after conversion to the corresponding azide, to a Curtius rearrangement to yield, after hydrolysis, an amine of formula (VII):

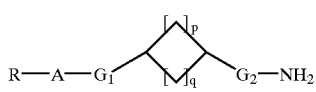 (VII)

wherein R, A, $G_1$, $G_2$, p and q are as defined hereinabove, which is either:

reacted with an acyl chloride $ClCOR^1_a$ or the corresponding mixed or symmetric anhydride wherein $R^1_a$ is as defined hereinabove to yield a compound of formula (I/c), a particular case of the compounds of formula (I):

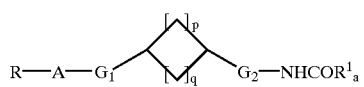 (I/c)

wherein R, A, $G_1$, $G_2$, $R^1_a$, p and q are as defined hereinabove, followed optionally by the action of a compound of formula (VIII):

$R_a$—J (VIII)

wherein $R_a$ is as defined hereinabove and J represents a leaving group, such as a halogen atom or a tosyl group, to yield a compound of formula (I/d), a particular case of the compounds of formula (I):

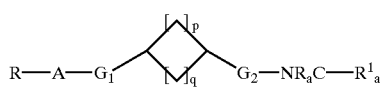 (I/d)

wherein R, A, $G_1$, $G_2$, $R_a$, $R^1_a$, p and q are as defined hereinabove,
the totality of the compounds (I/c) and (I/d) constituting the compounds of formula (I/e), a particular case of the compounds of formula (I):

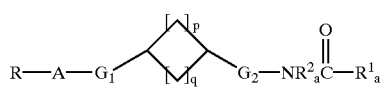 (I/e)

wherein R, A, $G_1$, $G_2$, $R^1_a$, $R^2_a$, p and q are as defined hereinabove,
which compounds of formula (I/e) may be subjected to the action of a thionisation agent, such as Lawesson's reagent, for example, to yield a compound of formula (I/f), a particular case of the compounds of formula (I):

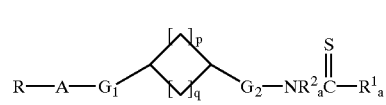 (I/f)

wherein R, A, $G_1$, $G_2$, $R^1_a$, $R^2_a$, p and q are as defined hereinabove,
or
subjected to the action of a compound of formula (IX):

Q=C=N—$R^1_a$ (IX)

wherein Q and $R^1_a$ are as defined hereinabove, followed optionally by the action of a compound of formula (VIII) to yield a compound of formula (I/g), a particular case of the compounds of formula (I):

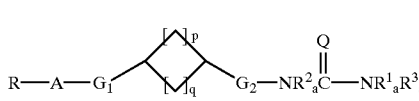 (I/g)

wherein R, A, $G_1$, $G_2$, $R^1_a$, $R^2_a$, $R^3_a$, Q, p and q are as defined hereinabove,
which compounds (I/a) to (I/g) constitute the totality of the compounds of formula (I) and may be purified according to a conventional separation technique, are converted, if desired, into their addition salts with a pharmaceutically acceptable acid or base, and optionally separated into their isomers according to a conventional separation technique.

The starting compounds (VI) are either commercial compounds or are readily accessible to the person skilled in the art by conventional chemical reactions or by chemical reactions described in the literature.

The compounds of the invention and pharmaceutical compositions containing them have proved to be useful in the treatment of disorders of the melatoninergic system.

Pharmacological study of the compounds of the invention has in fact demonstrated that they are atoxic, have a very high selective affinity for melatonin receptors and have substantial activity on the central nervous system and, in particular, therapeutic properties in respect of sleep disorders, anxiolytic, antipsychotic and analgesic properties, as well as properties in respect of microcirculation, have been found, enabling it to be established that the compounds of the invention are useful in the treatment of stress, sleep disorders, anxiety, seasonal affective disorder, cardiovascular pathologies, pathologies of the digestive system, insomnia and fatigue due to jetlag, schizophrenia, panic attacks, melancholia, appetite disorders, obesity, insomnia, psychotic disorders, epilepsy, diabetes, Parkinson's disease, senile dementia, various disorders associated with normal or pathological ageing, migraine, memory loss, Alzheimer's disease, and in cerebral circulation disorders. In another field of activity, it appears that the compounds of the invention can be used in the treatment of sexual dysfunctions, have ovulation-inhibiting and immunomodulating properties and are capable of being used in the treatment of cancers.

The compounds will preferably be used in the treatment of seasonal affective disorder, sleep disorders, cardiovascular pathologies, insomnia and fatigue due to jetlag, appetite disorders and obesity.

For example, the compounds will be used in the treatment of seasonal affective disorder and sleep disorders.

The present invention relates also to pharmaceutical compositions containing at least one compound of formula (I) on its own or in combination with one or more pharmaceutically acceptable excipients.

Among the pharmaceutical compositions according to the invention there may be mentioned more especially those that are suitable for oral, parenteral, nasal, per- or transcutaneous, rectal, perlingual, ocular or respiratory administration and especially tablets or dragees, sublingual tablets, sachets, paquets, gelatin capsules, glossettes, lozenges, suppositories, creams, ointments, dermal gels, and drinkable or injectable ampoules.

The dosage varies according to the sex, age and weight of the patient, the route of administration, the nature of the therapeutic indication, or any associated treatments and ranges from 0.01 mg to 1 g per 24 hours in 1 or more administrations.

The following Examples illustrate the invention and do not limit it in any way. The following Preparations yield synthesis intermediates for use in the preparation of the compounds of the invention.

Preparation 1

Trans-2-(7-methoxy-1-naphthyl)-1-cyclopropanamine

Step A: (7-Methoxy-1-naphthyl)methyl Acetate

In a 2 liter flask, 48.6 g (0.225 mol) of [7-methoxy(naphth-1-yl)]acetic acid are dissolved in a mixture of 700 ml benzene/300 ml acetic acid and refluxed under argon in order to degas the mixture. 100 g (1 eq) of lead tetraacetate are added at room temperature. The reaction mixture is heated at 60–70° C., at which temperature there is strong evolution of gas (release of $CO_2$), followed by 30 minutes' at boiling temperature. The reaction mixture is concentrated in vacuo and taken up while hot in $CH_2Cl_2$ (200 ml); 500 ml of ether are added slowly with stirring. The substantial amount of creamy white precipitate which forms is filtered off over Celite and rinsed with ether. The ethereal phase is then rendered basic by means of an ice-cold solution of 5% sodium hydrogen carbonate, neutralised with water, dried over $Na_2SO_4$ and concentrated under reduced pressure to yield an oil which recrystallises slowly when cold.

Step B: (7-Methoxy-1-naphthyl)methanol 34.5 g (0.15 mol) of the compound obtained in Step A are dissolved in 300 ml of methanol. 35 g (4 eq) of potassium hydroxide dissolved in 35 ml of water are added with vigorous stirring. After 3 hours at room temperature, the reaction mixture is hydrolysed over a mixture of ice/concentrated hydrochloric acid. The creamy white precipitate which forms is filtered off, washed several times with ice-cold water and dried over $P_2O_5$ using a dessicator. The title alcohol is recrystallised from a mixture of $CH_2Cl_2$/cyclohexane to yield white needles.

Step C: 7-Methoxy-1-naphthaldehyde 19.2 g (0.1 mol) of the compound obtained in Step B are dissolved in 300 ml of $CH_2Cl_2$. Under argon, 65 g (7.5 eq) of manganese oxide are added in three stages (t=0: 25 g, t=3 h :25 g, and t=24 h: 15 g). The alcohol is totally oxidised after a further 24 hours. The mixture is then filtered over Celite in order to remove the mineral compounds, rinsed with $CH_2Cl_2$ and then filtered over silica to yield an oil which solidifies on cooling.

Step D: Ethyl 3-(7-methoxy-1-naphthyl)-2-propenoate 2 g (10.7 mmol) of the compound obtained in Step C in 20 ml of anhydrous THF are placed in the presence of 515 mg (1.2 eq) of NaH (60% in oil) in 25 ml of anhydrous THF and 2.5 ml (1.2 eq) of triethyl phosphonoacetate. 3 hours' stirring at room temperature and gentle refluxing overnight yield a dark-coloured oil.

Step E: 3-(7-Methoxy-1-naphthyl)-2-propenoic Acid 8.4 g (32.8 mmol) of the ester obtained in Step D dissolved in 150 ml of ethanol in the presence of 40 ml of 2N sodium hydroxide solution are stirred for 3 hours at room temperature and overnight at reflux to yield the title acid in the form of a white solid.

Step F: N-Methoxy-N-methyl-3-(7-methoxy-1-naphthyl)-2-propenamide

The acid chloride obtained starting from 6.5 g (28.5 mmol) of the acid obtained in Step E and 5 ml of oxalyl chloride are added dropwise to a suspension of N,O-dimethylhydroxylamine chloride (5.6 g) in a mixture of $CH_2Cl_2/H_2O$ in the presence of 3 g of $Na_2CO_3$. The protected acid is obtained in the form of a pale yellow solid.

Step G: Trans-N-methoxy-N-methyl-2-(7-methoxy-1-naphthyl)-1-cyclopropanecarboxamide 5.8 g (21.4 mmol) of the compound obtained in Step F dissolved in 30 ml of DMSO are added to a suspension of ylid produced starting from 10.6 g (2 eq) of $Me_3SOI$ dissolved while hot in 50 ml of DMSO and 1.25 g of NaH. After 15 hours' stirring at room temperature and 4 hours at 50° C., the title cyclopropane amide is obtained in the form of a brown oil.

Step H: Trans-2-(7-methoxy-1-naphthyl)-1-cyclopropanecarboxylic Acid 6 g (21 mmol) of the compound obtained in Step G in 50 ml of anhydrous ether and 15.4 g of potassium tert-butylate are stirred for 2 days at room temperature. 3.2 g of a light brown solid are collected and reacted without purification.

Step I: Trans-2-(7-methoxy-1-naphthyl)-1-cyclopropanamine 1.5 g (6.2 mmol) of the acid obtained in Step H and 770 μl (1.3 eq) of ethyl chloroformate in the presence of triethylamine in acetone yield the mixed anhydride which is then treated with 550 mg (1.3 eq) of sodium azide. The acyl azide is then subjected to a rearrangement in 40 ml of anhydrous toluene at 80° C. to yield the isocyanate. The isocyanate is stirred for 36 hours at room temperature in an aqueous solution of 20% hydrochloric acid to yield the title amine.

The following Preparations are obtained by the same procedure:

Preparation 2 trans-2-(2,7-Dimethoxy-1-naphthyl)-1-cyclopropanamine

Preparation 3 trans-2-(2-Methoxy-1-naphthyl)-1-cyclopropanamine

Preparation 4 trans-2-(5-Methoxybenzo[b]furan-3-yl)-1-cyclopropanamine

Preparation 5 trans-2-(5-Methoxybenzo[b]thiophen-3-yl)-1-cyclopropanamine

Preparation 6 trans-2-(5-Methoxy-1H-pyrrolo[2,3-b]pyridin-3-yl)-1-cyclopropanamine

Preparation 7 trans-2-(5-Methoxy-2-phenylbenzo[b]furan-3-yl)-1-cyclopropanamine

Preparation 8 trans-2-(5-Methoxy-2-benzylbenzo[b]furan-3-yl)-1-cyclopropanamine

Preparation 9 trans-2-(5-Ethylbenzo[b]thiophen-3-yl)-1-cyclopropanamine

Preparation 10 trans-2-(5-Methoxy-2-phenylbenzo[b]thiophen-3-yl)-1-cyclopropanamine

Preparation 11 trans-2-(5-Methoxy-2-benzylbenzo[b]thiophen-3-yl)-1-cyclopropanamine

Preparation 12 trans-2-(7-Methoxy-3-phenyl-1-naphthyl)-1-cyclopropanamine

Preparation 13 trans-2-{7-Methoxy-3-[3-(trifluoromethyl)phenyl]-1-naphthyl}-1-cyclopropanamine

Preparation 14 trans-2-(5-Methoxy-2-phenyl-1H-pyrrolo[2,3-b]pyridin-3-yl)-1-cyclopropanamine

Preparation 15 trans-2-(2,3-Dihydro-1H-benzo[f]chromen-10-yl)-1-cyclopropanamine

Preparation 16 trans-2-(8,9-Dihydro-7H-furo[3,2-f]chromen-1-yl)-1-cyclopropanamine

Preparation 17 trans-2-(2-Methoxy-1-naphthyl)-1-cyclopropanecarbonitrile

Step A: 3-(2-Methoxy-1-naphthyl)-2-propenenitrile

Starting from 5 g (26.85 mmol) of 2-methoxynaphthaldehyde in 30 ml of anhydrous THF in the presence of 1.3 g (1.2 eq) of NaH (60% in oil) in 15 ml of anhydrous THF and 6.5 ml (1.2 eq) of diethyl cyanomethylphosphonate, the title product is obtained in the form of a white solid.

Step B: Trans-2-(2-methoxy-1-naphthyl)-1-cyclopropanecarbonitrile 5 g (23.9 mmol) of the compound obtained in Step A dissolved in 50 ml of DMSO are added dropwise to the ylid formed starting from 7.9 g (1.5 eq) of trimethylsulphoxonium iodide and 1.15 g (1.2 eq) of NaH (60% suspension in oil) in 20 ml of DMSO. The title compound is obtained in the form of an oil and is purified by chromatography over silica gel (eluant: $CH_2Cl_2$/i-PrOH 98/2).

The following Preparations are obtained by the same procedure:

Preparation 18 trans-2-(2,7-Dimethoxy-1-naphthyl)-1-cyclopropanecarbonitrile

Preparation 19 trans-2-(7-Methoxy-1-naphthyl)-1-cyclopropanecarbonitrile

Preparation 20 trans-2-(7-Methoxy-3-phenyl-1-naphthyl)-1-cyclopropanecarbonitrile

Preparation 21 trans-2-(5-Methoxy-2-phenylbenzo[b]furan-3-yl)-1-cyclopropanecarbonitrile

Preparation 22 trans-2-(5-Ethylbenzo[b]thiophen-3-yl)-1-cyclopropanecarbonitrile

Preparation 23 trans-2-{5-Methoxy-2-[3-(trifluoromethyl)benzyl]benzo[b]-thiophen-3-yl}-1-cyclopropanecarbonitrile

Preparation 24 trans-2-(5-Methoxy-2-phenyl-1H-pyrrolo[2,3-b]pyridin-3-yl)-1-cyclopropanecarbonitrile

Preparation 25 trans-2-(2,3-Dihydro-1H-benzo[f]chromen-10-yl)-1-cyclopropanecarbonitrile

Preparation 26 trans-2-(8,9-Dihydro-7H-furo[3,2-f]chromen-1-yl)-1-cyclopropanecarbonitrile

Preparation 27

3-(2-Methoxy-1-naphthyl)cyclobutanamine

A solution of 0.1 mol of cyclobutenone in 50 ml of THF is added dropwise to the Grignard reagent formed starting from 1-bromo-2-methoxynaphthalene (0.1 mol) and 2.5 g of magnesium in 200 ml of THF. The reaction mixture is stirred. At the end of the reaction, the mixture is quenched with 3N HCl and stirred for 1 hour after dilution in 200 ml of ether. Following extraction with ether and concentration in vacuo of the organic phase, the corresponding cyclobutanone is obtained and is redissolved with hydroxylamine. After the oxime has formed, the mixture is subjected to hydrogenation over Raney nickel to yield the title amine.

Preparations 28 and 29 are obtained by following the procedure described in Preparation 27, starting from the appropriate substrates.

Preparation 28

3-(2,7-Dimethoxy-1-naphthyl)cyclohexanamine

Preparation 29

3-(2,7-Dimethoxy-1-naphthyl)cyclopentanamine

Preparation 30

2-[(7-Methoxy-1-naphthyl)methyl]cyclopropanamine

The procedure is as for Preparation 1, Steps D-I starting from 2-(7-methoxy-1-naphthyl)acetaldehyde.

Preparation 31

2-[(7-Methoxy-3-phenyl-1-naphthyl)methyl]cyclopropanecarbonitrile

The procedure is as for Preparation 17 starting from 2-(7-methoxy-3-phenyl)-acetaldehyde.

Preparation 32

2-(8,9-Dihydro-7H-furo[3,2-f]chromen-1-ylmethyl)-cyclopropanecarboxylic Acid Step A: 2-(8,9-Dihydro-7H-furo[3,2-f]chromen-1-ylmethyl) cyclopropanecarbonitrile The procedure is as for Preparation 17 starting from 2-(8,9-dihydro-7H-furo[3,2-f]-chromen-1-yl)acetaldehyde.

Step B:

2-(8,9-Dihydro-7H-furo[3,2-f]chromen-1-ylmethyl) cyclopropanecarboxylic Acid

The compound obtained in Step A is hydrolysed in an acidic or basic medium.

Preparations 33 and 34 are obtained by proceeding as in Preparation 32.

Preparation 33

2-{[5-Methoxy-2-(3-methoxyphenyl)-1-benzofuran-3-yl]methyl}cyclopentanecarboxylic Acid

Preparation 34

2-[(5-Methoxyfuro[2,3-b]pyridin-3-yl)methyl]cyclobutanecarboxylic Acid

Preparations 35 to 38 are obtained by proceeding as in Preparation 1, replacing Step G by a cycloaddition with the appropriate substrate.

Preparation 35

2-(5-Ethyl-1-benzothiophen-3-yl)cyclohexylamine

Preparation 36

2-(5-Ethyl-1-benzothiophen-3-yl)cyclobutylamine

Preparation 37

2-(8,9-Dihydro-7H-furo[3,2-]chromen-1-yl)cyclobutylamine

Preparation 38

2-(5-Methoxy-1H-pyrrolo[3,2-b]pyridin-3-yl)cyclopentylamine

EXAMPLE 1

N-[trans-2-(7-Methoxy-1-naphthyl)-1-cyclopropyl]acetamide 350 mg of the compound obtained in Preparation 1 are dissolved in a mixture of $CH_2Cl_2/H_2O$ (5:5 ml) in the presence of sodium carbonate. 247 µl (1.5 eq) of acetic anhydride are added dropwise at 0° C. The resulting crude amide is purified by chromatography over a column of silica gel (eluant: $CH_2Cl_2$/i-PrOH 95:5) to yield a white solid which is recrystallised from a mixture of hexane/$CH_2Cl_2$.

Melting point: 136° C.; Elemental microanalysis:

|  | % C | % H | % N |
|---|---|---|---|
| theoretical + 1/5 $H_2O$ | 74.31 | 6.62 | 5.41 |
| experimental | 74.32 | 6.69 | 5.44 |

EXAMPLE 2

N-[trans-2-(7-Methoxy-1-naphthyl)-1-cyclopropyl]propanamide 400 mg of the compound obtained in Preparation 1 are dissolved in a mixture of $CH_2Cl_2/H_2O$ (5:5 ml), in the presence of sodium carbonate. 1.5 eq of propanoic anhydride are added dropwise at 0° C. The resulting crude amide is purified by chromatography over a column of silica gel (eluant: $CH_2Cl_2$/i-PrOH 95:5) to yield a white solid which is recrystallised from a mixture of hexane/$CH_2Cl_2$.

Melting point: 125° C.; Elemental microanalysis:

|  | % C | % H | % N |
|---|---|---|---|
| theoretical | 75.55 | 6.92 | 5.34 |
| experimental | 75.15 | 7.01 | 5.14 |

EXAMPLE 3

N-[trans-2-(7-Methoxy-1-naphthyl)-1-cyclopropyl]butanamide 150 mg (0.7 mmol) of the compound obtained in Preparation 1 are dissolved in 10 ml of anhydrous $CH_2Cl_2$, in the presence of 146 μl (1.5 eq) of triethylamine. At 0° C. under argon, 87 μl (1.2 eq) of butyric acid chloride are added dropwise. After stirring for one hour, the reaction mixture is hydrolysed and the amide is extracted with $CH_2Cl_2$. After chromatography over a column of silica gel (eluant: $CH_2Cl_2$/i-PrOH 95:5), the resulting white solid is recrystallised from a mixture of hexane/$CH_2Cl_2$.

Melting point: 119° C.; Elemental microanalysis:

|  | % C | % H | % N |
|---|---|---|---|
| theoretical | 76.32 | 7.42 | 4.94 |
| experimental | 76.17 | 7.57 | 4.96 |

EXAMPLE 4

N-[trans-2-(7-Methoxy-1-naphthyl)-1-cyclopropyl]cyclopropanecarboxamide 180 mg (0.7 mmol) of the compound obtained in Preparation 1 are dissolved in 10 ml of anhydrous $CH_2Cl_2$, in the presence of 141 μl (1.5 eq) of triethylamine. At 0° C., under argon, 84 μl (1.2 eq) of cyclopropanecarbonyl chloride are added dropwise. After stirring for one hour, the reaction mixture is hydrolysed and the amide is extracted with $CH_2Cl_2$. After chromatography over a column of silica gel (eluant: $CH_2Cl_2$/i-PrOH 95:5), the resulting white solid is recrystallised from a mixture of hexane/$CH_2Cl_2$.

Melting point: 165° C.; Elemental microanalysis:

|  | % C | % H | % N |
|---|---|---|---|
| theoretical | 76.84 | 6.80 | 4.98 |
| experimental | 76.29 | 6.92 | 4.97 |

EXAMPLE 5

N-[trans-2-(2,7-Dimethoxy-1-naphthyl)-1-cyclopropyl]acetamide 400 mg (1.64 mmol) of the compound obtained in Preparation 2 are dissolved in a mixture of $CH_2Cl_2$/$H_2O$ (10:10 ml), in the presence of sodium carbonate. 200 μl (1.5 eq) of acetic anhydride are added dropwise at 0° C. The resulting crude amide is purified by chromatography over silica (eluant: $CH_2Cl_2$/i-PrOH 90:10) and yields a white solid which is recrystallised from a mixture of hexane/$CH_2Cl_2$.

Melting point: 128° C.; Elemental microanalysis:

|  | % C | % H | % N |
|---|---|---|---|
| theoretical | 71.49 | 6.66 | 4.90 |
| experimental | 70.99 | 6.74 | 4.88 |

EXAMPLE 6

N-[trans-2-(2,7-Dimethoxy-1-naphthyl)-1-cyclopropyl]propanamide 500 mg (2 mmol) of the compound obtained in Preparation 2 are dissolved in a mixture of $CH_2Cl_2$/$H_2O$ (10:10 ml), in the presence of sodium carbonate. 215 μl (1.2 eq) of propionic anhydride are added dropwise at 0° C. The resulting crude amide is purified by chromatography over silica (eluant: $CH_2Cl_2$/i-PrOH 98:2) and yields a white solid which is recrystallised from a mixture of hexane/$CH_2Cl_2$.

Melting point: 135° C.; Elemental microanalysis:

|  | % C | % H | % N |
|---|---|---|---|
| theoretical + 1/3 $H_2O$ | 70.81 | 6.93 | 4.59 |
| experimental | 70.86 | 7.00 | 4.58 |

EXAMPLE 7

N-[trans-2-(2,7-Dimethoxy-1-naphthyl)-1-cyclopropyl]butanamide 100 mg of the compound obtained in Preparation 2 are dissolved in a mixture of $CH_2Cl_2$/$H_2O$ (10:10 ml), in the presence of sodium carbonate. 43 μl (1.2 eq) of butyric anhydride are added dropwise at 0° C. The resulting crude amide is purified by chromatography over silica (eluant: $CH_2Cl_2$/i-PrOH 95:5) to yield an oil which crystallises slowly at room temperature and is recrystallised from a mixture of hexane/$CH_2Cl_2$.

EXAMPLE 8

N-[trans-2-(2-Methoxy-1-naphthyl)-1-cyclopropyl]acetamide 500 mg of the compound obtained in Preparation 3 are dissolved in a mixture of $CH_2Cl_2$/$H_2O$ (10:10 ml), in the presence of sodium carbonate. 332 μl (1.5 eq) of acetic anhydride are added dropwise at 0° C. The resulting crude amide is purified by chromatography over a column of silica gel (eluant: $CH_2Cl_2$/i-PrOH 90:10) and yields an oil which crystallises slowly in the form of white crystals recrystallised from a mixture of hexane/$CH_2Cl_2$.

Melting point: 155° C.;

|  | % C | % H | % N |
|---|---|---|---|
| theoretical | 75.29 | 6.66 | 5.49 |
| experimental | 75.35 | 6.65 | 5.39 |

EXAMPLE 9

N-[trans-2-(2-Methoxy-1-naphthyl)-1-cyclopropyl]propanamide 450 mg of the compound obtained in Preparation 3 are dissolved in a mixture of $CH_2Cl_2$/$H_2O$ (10:10 ml), in the presence of sodium carbonate. 400 μl (1.5 eq) of propionic anhydride are added dropwise at 0° C. The resulting crude amide is purified by chromatography over silica (eluant: $CH_2Cl_2$/i-PrOH 95:5) and yields an oil which crystallises slowly in the form of light beige crystals recrystallised from a mixture of hexane/$CH_2Cl_2$.

Melting point: 144° C.;

|  | % C | % H | % N |
|---|---|---|---|
| theoretical | 75.55 | 6.92 | 5.34 |
| experimental | 75.72 | 6.92 | 5.17 |

EXAMPLE 10

N-[trans-2-(2-Methoxy-1-naphthyl)-1-cyclopropyl]butanamide 400 mg of the compound obtained in Preparation 3 are dissolved in a mixture of $CH_2Cl_2$/$H_2O$ (10:10 ml), in the presence of sodium carbonate. 460 μl (1.5 eq) of butyric anhydride are added dropwise at 0° C. The resulting crude amide is purified by chromatography over silica (eluant: $CH_2Cl_2$/i-PrOH 95:5) to yield a white solid which is recrystallised from a mixture of hexane/$CH_2Cl_2$.

Melting point: 113° C.; Elemental microanalysis:

|  | % C | % H | % N |
|---|---|---|---|
| theoretical | 76.32 | 7.42 | 4.94 |
| experimental | 76.23 | 7.40 | 4.94 |

EXAMPLE 11

N-[trans-2-(2-Methoxy-1-naphthyl)-1-cyclopropylmethyhyl]acetamide 1.6 ml (5 eq) of acetic anhydride and a spatula of Raney nickel are added to 700 mg (3.1 mmol) of the compound obtained in Preparation 17 dissolved in 20 ml of THF. After 24 hours at room temperature under a hydrogen atmosphere, the residue is chromatographed over a column of silica gel (eluant $CH_2Cl_2$; $CH_2Cl_2$/i-PrOH 95:5). The expected acetamide is obtained in the form of an oil which crystallises to yield a white solid which is recrystallised from a mixture of $CH_2Cl_2$/hexane.

Melting point: 96° C.;

EXAMPLE 12

N-[trans-2-(2-Methoxy-1-naphthyl)-1-cyclopropylmethyl]-propanamide 1 ml (3 eq) of propionic anhydride and a spatula of Raney nickel are added to 600 mg (3.1 mmol) of the compound obtained in Preparation 17 dissolved in 20 ml of THF. After 5 hours at 50° C. under a hydrogen atmosphere, the residue is chromatographed over a column of silica gel (eluant $CH_2Cl_2$; $CH_2Cl_2$/i-PrOH 98:2). The title compound is obtained in the form of a colourless oil.

Elemental microanalysis:

|  | % C | % H | % N |
|---|---|---|---|
| theoretical + 1/5 $H_2O$ | 75.34 | 7.38 | 4.88 |
| experimental | 75.35 | 7.66 | 4.67 |

EXAMPLE 13

N-[trans-2-(2-Methoxy-1-naphthyl)-1-cyclopropylmethyl]-butanamide 1.2 ml (3 eq) of butyric anhydride and a spatula of Raney nickel are added to 550 mg (2.5 mmol) of the compound obtained in Preparation 17 dissolved in 20 ml of THF. After 4 hours at 50° C. under a hydrogen atmosphere, the residue is chromatographed over a column of silica gel (eluant $CH_2Cl_2$; $CH_2Cl_2$/i-PrOH 98:2). The title compound is obtained in the form of a colourless oil.

Elemental microanalysis:

|  | % C | % H | % N |
|---|---|---|---|
| theoretical + 1/4 $H_2O$ | 75.60 | 7.68 | 4.64 |
| experimental | 75.63 | 7.86 | 4.37 |

Examples 14 to 17 are obtained by proceeding as in Example 1 starting from the appropriate Preparations

EXAMPLE 14

N-[trans-2-(5-Methoxybenzo[b]furan-3-yl)cyclopropyl]acetamide
Starling Material: Preparation 4

EXAMPLE 15

N-[trans-2-(5-Methoxy-2-phenylbenzo[b]furan-3-yl)cyclopropyl]acetamide
Starting Material: Preparation 7

EXAMPLE 16

N-[trans-(7-Methoxy-3-phenyl-1-naphthyl)-1-cyclopropyl]-acetamide
Starting Material: Preparation 12

EXAMPLE 17

N-[trans-2-(8,9-dihydro-7H-furo[3,2-f]chromen-1-yl)-1-cyclopropyl]acetamide
Starting Material: Preparation 16

Examples 18 to 20 are obtained by proceeding as in Example 2 starting from the appropriate Preparations:

EXAMPLE 18

N-[trans-2-(5-Methoxy-1H-pyrrolo[2,3-b]pyridin-3-yl)-1-cyclopropyl]propanamide
Starting Material: Preparation 6

EXAMPLE 19

N-[trans-2-(5-Methoxybenzo[b]thiophen-3-yl)-1-cyclopropyl]-propanamide
Starting Material: Preparation 9

EXAMPLE 20

N-[trans-2-{7-Methoxy-3-[3-(trifluoromethyl)
phenyl]-1-naphthyl}-cyclopropyl]propanamide Starting Material: Preparation 13

Examples 21 to 23 are obtained by proceeding as in Example 3 starting from the appropriate Preparations:

EXAMPLE 21

N-[trans-2-(5-Methoxybenzo[b]thiophen-3-yl)
cyclopropyl]-butanamide

Starting Material: Preparation 5

EXAMPLE 22

N-[trans-2-(5-Methoxy-2-phenylbenzo[b]thiophen-
3-yl)cyclopropyl]butanamide

Starting material: Preparation 10

EXAMPLE 23

N-[trans-2-(5-Methoxy-2-phenyl-1H-pyrrolo[2,3-b]
pyridin-3-yl)cyclopropyl]butanamide Starting Material: Preparation 14

Examples 24 to 26 are obtained by proceeding as in Example 4 starting from the appropriate Preparations

EXAMPLE 24

N-[trans-2-(5-Methoxy-2-phenylbenzo[b]furan-3-yl)
cyclopropyl]-1-cyclopropanecarboxamide Starting Material: Preparation 7

EXAMPLE 25

N-[trans-2-(5-Methoxy-2-benzylbenzo[b]thiophen-3-
yl) cyclopropyl]-1-cyclopropanecarboxamide Starting Material: Preparation 11

EXAMPLE 26

N-[trans-2-(2,5-dihydro-1H-benzo[f]chromen-10-yl)
cyclopropyl]-1-cyclopropanecarboxamide Starting Material: Preparation 15

Examples 27 to 30 are obtained by proceeding as in Example 11 starting from the appropriate Preparations:

EXAMPLE 27

N-[trans-2-(2-Methoxy-1-naphthyl)-1-
cyclopropylmethyl]acetamide

Starting Material: Preparation 17

EXAMPLE 28

N-[trans-2-(5-Methoxy-3-phenyl-1-naphthyl)-1-
cyclopropylmethyl]-acetamide

Starting Material: Preparation 20

EXAMPLE 29

N-[trans-2-{5-Methoxy-2-[3-(trifluoromethyl)
benzyl]benzo[b]-thiophen-3-yl}methyl]acetamide Starting Material: Preparation 23

EXAMPLE 30

N-{trans-[2-(2,3-Dihydro-1H-benzo [f]chromen-10-
yl)-1-cyclopropyl]-methyl}acetamide Starting Material: Preparation 25

Examples 31 to 34 are obtained by proceeding as in Example 12 starting from the appropriate Preparations:

EXAMPLE 31

N-[trans-(2,7-Dimethoxy-1-naphthyl)-1-
cyclopropylmethyl]-propanamide

Starting Material: Preparation 18

EXAMPLE 32

N-[trans-2-(5-Methoxy-2-phenylbenzo[b]furan-3-yl-
cyclopropyl-methyl]propanamide Starting Material: Preparation 21

EXAMPLE 33

N-{trans-[2-(5-Methoxy-1-methyl-2-phenyl-1H-
pyrrolo[2,3-b]-pyridin-3-yl)cyclopropyl]
methyl}propanamide Starting Material: Preparation 24

EXAMPLE 34

N-{trans-[2-(8,9-Dihydro-7H-furo[3,2-f]chromen-1-
yl)cyclopropyl]-methyl}propanamide Starting Material: Preparation 26

Examples 35 and 36 are obtained by proceeding as in Example 13 starting from the appropriate Preparations:

EXAMPLE 35

N-[trans-2-(7-Methoxy-1-naphthyl)
cyclopropylmethyl]butanamide

Starting Material: Preparation 19

EXAMPLE 36

N-[trans-2-(5-Ethyl-benzo[b]thiophen-3-yl)
cyclopropylmethyl]-butanamide

Starting material: Preparation 22

EXAMPLE 37

N-[3-(2-Methoxy-1-naphthyl)cyclobutyl]acetamide

The procedure is as in Example 1 starting from the compound obtained in Preparation 27.

EXAMPLE 38

N-[3-(2,7-Dimethoxy-1-naphthyl)cyclohexyl]
propanamide

The procedure is as in Example 2 starting from the compound obtained in Preparation 28.

EXAMPLE 39

N-[3-(2,7-Dimethoxy-1-naphthyl)cyclopentyl]-N'-
methylurea

The title product is obtained by condensation of methyl isocyanate with the compound obtained in Preparation 29.

EXAMPLE 40

N-{2-[(7-Methoxy-1-naphthyl)methyl]
cyclopropyl}butanamide

The procedure is as in Example 3 starting from the compound obtained in Preparation 30.

EXAMPLE 41

N-({2-[(7-Methoxy-3-phenyl-1-naphthyl)methyl]
cyclopropyl}-methyl)propanamide

The procedure is as in Example 12 starting from the compound obtained in Preparation 31.

EXAMPLE 42

2-(8,9-Dihydro-7H-furo[3,2-f]chromen-1-ylmethyl)-
N-methyl-cyclopropanecarboxamide The title product is obtained by condensing N-methylamine with the compound obtained in Preparation 32 in the presence of a coupling agent.

EXAMPLE 43

N-Allyl-2-{[5-Methoxy-2-(3-methoxyphenyl)-1-
benzofuran-3-yl]methyl}cyclopentanecarboxamide The title product is obtained by condensing N-allylamine with the compound obtained in Preparation 33 in the presence of a coupling agent.

EXAMPLE 44

N-(Bromoethyl)-2-[(5-Methoxyfuro[2,3-b]pyridin-3-
yl)methyl]-cyclobutanecarboxamide The title product is obtained by condensing N-(bromomethyl)amine with the compound obtained in Preparation 34 in the presence of a coupling agent.

EXAMPLE 45

N-{2-[(5-Ethyl-1-benzothiophen-3-yl)methyl]
cyclohexyl}-butanamide

The procedure is as in Example 2 starting from the compound obtained in Preparation 35.

EXAMPLE 46

N-[2-(5-Ethyl-1-benzothiophen-3-yl)cyclobutyl]
cyclopropanecarboxamide

The procedure is as in Example 4 starting from the compound obtained in Preparation 36.

EXAMPLE 47

N-[2-(8,9-Dihydro-7H-furo[3,2-f]chromen-1-yl)
cyclobutyl]-2-methylpropanamide

The procedure is as in Example 4, replacing cyclopropanecarbonyl chloride by 2-methylpropanoic acid chloride.

EXAMPLE 48

N-[2-(5-Methoxy-1H-pyrrolo[3,2-b]pyridin-3-yl)
cyclopentyl]-butanamide

The procedure is as in Example 2 starting from the compound obtained in Preparation 38.

PHARMACOLOGICAL STUDY

Example A

Acute Toxicity Study

Acute toxicity was evaluated after oral administration to groups each comprising 8 mice (26±2 grams). The animals were observed at regular intervals during the course of the first day, and daily for the two weeks following treatment. The $LD_{50}$ (dose that causes the death of 50% of the animals) was evaluated and demonstrated the low toxicity of the compounds of the invention.

Example B

Melatonin Receptor Binding Study on Pars Tuberalis Cells of Sheep

Melatonin receptor binding studies of the compounds of the invention were carried out according to conventional techniques on pars tuberalis cells of sheep. The pars tuberalis of the adenohypophysis is in fact characterised in mammals by a high density of melatonin receptors (Journal of Neuroendocrinology, 1, pp. 1–4, 1989).

Protocol

1) Sheep pars tuberalis membranes are prepared and used as target tissue in saturation experiments to determine the binding capacities and affinities for 2-[$^{125}$I]-iodomelatonin.
2) Sheep pars tuberalis membranes are used as target tissue in competitive binding experiments using the various test compounds in comparison with melatonin.

Each experiment is carried out in triplicate and a range of different concentrations is tested for each compound. The results, after statistical processing, enable the binding affinities of the compound tested to be determined.

Results

The compounds of the invention appear to have a strong affinity for melatonin receptors.

Example C

Melatonin $Mt_1$ and $MT_2$ Receptor Binding Study

The $mt_1$ or $MT_2$ receptor binding experiments are carried out using 2-[$^{125}$I]-melatonin as reference radioligand. The radioactivity retained is determined using a Beckman® LS 6000 liquid scintillation counter.

Competitive binding experiments are then carried out in triplicate using the various test compounds. A range of different concentrations is tested for each compound. The results enable the binding affinities of the compounds tested ($IC_{50}$) to be determined.

The $IC_{50}$ values found for the compounds of the invention show that the binding of the compounds tested is very strong for one or other of the $mt_1$ and $MT_2$ receptor sub-types, the values being in a range from 0.1 to 10 nM.

Example D

Four Plate Test

The products of the invention are administered by the oesophageal route to groups each comprising ten mice. One group is given syrup of gum. Thirty minutes after administration of the products to be studied, the animals are placed in cages in which the floor is composed of four metal plates. Each time the animal passes from one plate to another it receives a light electric shock (0.35 mA). The number of passages from one plate to another in one minute is recorded. After administration, the compounds of the invention significantly increase the number of passages from one plate to another, demonstrating the anxiolytic activity of the compounds of the invention.

Example E

Action of the Compounds of the Invention on the Circadian Rhythms of Locomotive Activity of the Rat The involvement of melatonin in influencing, by day/night alternation, the majority of physiological, biochemical and behavioural circadian rhythms has made it possible to establish a pharmacological model for research into melatoninergic ligands.

The effects of the compounds are tested in relation to numerous parameters and, in particular, in relation to the circadian rhythms of locomotive activity, which are a reliable indicator of the activity of the endogenous circadian clock.

In this study, the effects of such compounds on a particular experimental model, namely the rat placed in temporal isolation (permanent darkness), are evaluated.

Experimental protocol

One-month-old Long Evans male rats are subjected, as soon as they arrive at the laboratory, to a light cycle of 12 hours light per 24 hours (LD 12:12). After 2 to 3 weeks' adaptation, they are placed in cages fitted with a wheel connected to a to recording system in order to detect the phases of locomotive activity and thus monitor the nychthemeral (LD) or circadian (DD) rhythms.

As soon as the rhythms recorded show a stable pattern in the light cycle LD 12:12, the rats are placed in permanent darkness (DD).

Two to three weeks later, when the free course (rhythm reflecting that of the endogenous clock) is clearly established, the rats are given a daily administration of the compound to be tested.

The observations are made by means of visualisation of the rhythms of activity influence of the light rhythm on the rhythms of activity,
disappearance of the influence on the rhythms in permanent darkness,
influence of the daily administration of the compound; transitory or durable effect.

A software package makes it possible:
to measure the duration and intensity of the activity, the period of the rhythm of the animals during free course and during treatment,
possibly to demonstrate by spectral analysis the existence of circadian and non-circadian (for example ultradian) components.

Results:

The compounds of the invention clearly appear to allow powerful action on the circadian rhythm via the melatoninergic system.

Example

Anti-arrythmic Activity

Protocol (Ref: LAWSON J. W. et al. J. Pharmacol. Expert. Therap., 1968, 160, pp. 22–31)

The test substance is administered intraperitoneally to a group of 3 mice 30 minuutes before being subjected to anaesthesia with chloroform. The animals are then observed for 15 minutes. The absence of recording of arrhythmia and of cardiac frequencies higher than 200 beats/min (control: 400–480 beats/min) in at least two animals indicates significant protection.

Example G

Pharmaceutical Composition: Tablets

| | |
|---|---|
| 1000 tablets each comprising 5 mg of N-[trans 2-(7-methoxy-1-naphthyl)-1-cyclopropyl]acetamide (Example 1) | 5 g |
| Wheat starch | 20 g |
| Maize starch | 20 g |
| Lactose | 30 g |
| Magnesium stearate | 2 g |
| Silica | 1 g |
| Hydroxypropyl cellulose | 2 g |

We claim:
1. A compound selected from those of formula (I):

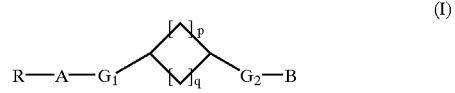

(I)

wherein
❖ A represents:
➢ a ring system of formula (II):

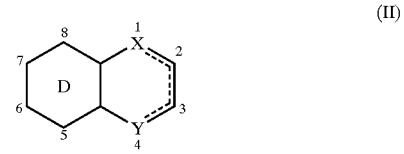

(II)

wherein X and Y, which may be identical or different, represent oxygen, sulphur or $CH_2$,
D represents a benzene ring or a naphthalene ring,
and the symbol ------- means that the bonds may be single or double, with the proviso that the valency of the atoms is respected,
wherein R substitutes either the ring system D or the ring containing X and Y, and $G_1$ substitutes the ring containing X and Y,
➢ or a ring system of formula (III):

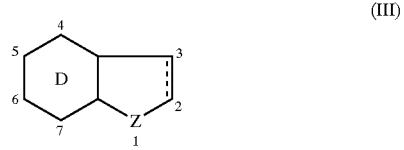

(III)

wherein Z represents oxygen, sulphur, $CH_2$, or $NR^1$ (wherein $R^1$ represents hydrogen, linear or branched $(C_1-C_6)$alkyl, aryl, or aryl-$(C_1-C_6)$alkyl in which the alkyl moiety is linear or branched),
D' represents a benzene ring or a pyridine ring, and the symbol ------- is as defined hereinabove,
wherein R substitutes the D' ring and $G_1$ substitutes the other ring,
it being understood that the ring systems of formula (II) or (III) may be substituted, in addition to R and $G_1$, by from one to three identical or different groups selected from $R_a$, $OR_a$, hydroxyl, $COR_a$, formyl, $COOR_a$, carboxyl, and $OCOR_a$,
wherein $R_a$ represents substituted or unsubstituted linear or branched $(C_1-C_6)$alkyl, substituted or unsubstituted linear or branched $(C_2-C_6)$alkenyl, substituted or unsubstituted linear or branched $(C_2-C_6)$alkynyl, linear or branched polyhalo-$(C_1-C_6)$alkyl, substituted or unsubstituted $(C_3-C_8)$-cycloalkyl, substituted or unsubstituted $(C_3-C_8)$cycloalkyl-$(C_1-C_6)$alkyl in which the alkyl moiety is linear or branched, substituted or unsubstituted $(C_3-C_8)$cycloalkenyl, substituted or unsubstituted $(C_3-C_8)$cycloalkenyl-$(C_1-C_6)$alkyl in which the alkyl moiety is linear or branched, aryl, aryl-$(C_1-C_6)$alkyl in which the alkyl moiety is linear or branched, heteroaryl, or heteroaryl-$(C_1-C_6)$alkyl in which the alkyl moiety is linear or branched, ❖R represents hydrogen, halogen, hydroxyl, SH, $R_a$, $OR_a$, or $S(O)_nR_a$, wherein n is 0, 1 or 2 and $R_a$ is as defined hereinabove, or forms, with the carbon atom carrying it and with an adjacent carbon atom, a ring of formula (IV):

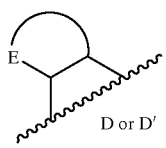

(IV)

wherein E represents oxygen or —$S(O)_n$— wherein n is as defined hereinabove, wherein the resulting ring contains 5 to 7 atoms, may contain one or more unsaturations and may be substituted by one or more groups selected from linear or branched $(C_1-C_6)$alkyl, linear or branched $(C_1-C_6)$ alkoxy, carboxy, linear or branched $(C_1-C_6)$alkoxy-carbonyl, hydroxy, and oxo, ❖$G_1$ and $G_2$, which may be identical or different, represent a single bond or an alkylene chain —$(CH_2)_t$— (wherein t is 1, 2, 3 or 4), unsubstituted or substituted by one or more identical or different radicals selected from hydroxy, carboxy, formyl, $R_a$, $OR_a$, $COOR_a$, $COR_a$ (wherein $R_a$ is as defined hereinabove), and halogen, ❖p is 0, 1, 2, 3 or 4, q is 0, 1, 2, 3 or 4, with $1 \leq p+q \leq 4$, ❖B represents —$NR^1_aC(Q)R^2_a$, —$NR^1_aC(Q)NR^2_aR^3_a$, or —$C(Q)NR^1_aR^2_a$, wherein, $R^1_a$, $R^2_a$ and $R^3_a$, which may be identical or different, can have any of the values of $R_a$ or may represent hydrogen, and Q represents oxygen or sulphur, it being understood that:

the term "substituted" applied to the terms "alkyl", "alkenyl", and "alkynyl" means that those are substituted by one or more identical or different radicals selected from hydroxy, linear or branched $(C_1-C_6)$ alkoxy, linear or branched $(C_1-C_6)$alkyl, linear or branched polyhalo-$(C_1-C_6)$alkyl, amino, and halogen, the term "substituted" applied to the terms "cycloalkyl", "cycloalkylalkyl", "cycloalkenyl", and "cycloalkenylalkyl", means that the cyclic moiety of those groups is substituted by one or more identical or different radicals selected from hydroxy, linear or branched $(C_1-C_6)$alkoxy, linear or branched $(C_1-C_6)$ alkyl, linear or branched polyhalo-$(C_1-C_6)$alkyl, amino, and halogen, "aryl" is understood to mean phenyl, naphthyl or biphenyl, or one of those groups substituted by one or more identical or different radicals selected from hydroxy, linear or branched $(C_1-C_6)$alkoxy, linear or branched $(C_1-C_6)$alkyl, linear or branched polyhalo-$(C_1-C_6)$alkyl, cyano, carboxy, linear or branched $(C_1-C_6)$alkoxy-carbonyl, nitro, amino, and halogen, "heteroaryl" is understood to mean a mono- or poly-cyclic aromatic containing 5 to 10 atoms and containing 1 to 3 hetero atoms selected from nitrogen, oxygen, and sulphur, or one of those groups substituted by one or more identical or different radicals selected from hydroxy, linear or branched $(C_1-C_6)$alkoxy, linear or branched $(C_1-C_6)$alkyl, linear or branched polyhalo-$(C_1-C_6)$alkyl, cyano, carboxy, linear or branched $(C_1-C_6)$alkoxy-carbonyl, nitro, amino, and halogen, with the proviso that:

when A represents a naphthalene unsubstituted or substituted by one methoxy or one methyl, $G_1$ and $G_2$ simultaneously represent a single bond, and B represents

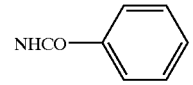

or NHCOMe, it is not possible to have (q=0 and p=4) or (q=4 and p=0), when $G_1$ represents a single bond and p+q=1, then A cannot represent a naphthalene substituted by one or more halogen, when A represents an indole substituted in the 2-position by

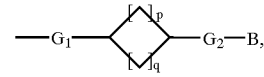

then B cannot represent an urea, when A represents an indole substituted in the 2-position by carboxyl or alkoxycarbonyl, p is 1 and q is 0 (or q is 1 and p is 0), and $G_1$ represents a single bond, then B cannot represent CONHAr wherein Ar represents aryl, their enantiomers and diastereoisomers, and addition salts thereof with a pharmaceutically-acceptable acid or base.

2. A compound of claim 1 wherein p is 1, 2, 3 or 4 and q is 0 (or p is 0 and q is 1, 2, 3 or 4).

3. A compound of claim 1 wherein p is 1 and q is 0 (or p is 0 and q is 1).

4. A compound of claim 3 wherein the R—A—$G_1$— and —$G_2$—B groups are in the trans configuration.

5. A compound of claim 1 wherein R represents $OR_a$, $SR_a$ or $R_a$.

6. A compound of claim 1 wherein R represents $OR_a$.

7. A compound of claims 1 wherein R forms, with the carbon atom carrying it and with an adjacent carbon atom, a ring of formula (IV).

8. A compound of claim 1 wherein A represents a ring system of formula (II) substituted in the 7-position by R and in the 1- or 2-position by $G_1$, A being unsubstituted or substituted (as well as by the substituents R and $G_1$) in the 2- or 3-position.

9. A compound of claim 1 wherein A represents a ring system of formula (III) substituted in the 5-position by R and in the 3-position by $G_1$, A being unsubstituted or substituted (in addition to the substituents R and $G_1$) in the 2-position.

10. A compound of claim 1 wherein $G_1$ represents a single bond and $G_2$ represents a single bond or $CH_2$.

11. A compound of claim 1 wherein B represents —NHCOR$_a$ or —CONHR$_a$.

12. A compound of claim 1 wherein A is substituted:

by a group of formula (V):

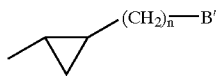   (V)

wherein n is 0 or 1 and B' represents —NHCOR$_a$ or —CONHR$_a$, by OR$_a$, SR$_a$, or R$_a$, and optionally by alkoxy, aryl, or arylalkyl.

13. A compound of claim 1 wherein A represents naphthalene, chroman, or benzochroman, substituted in the 1- or 2-position (formula II) by a group of formula (V):

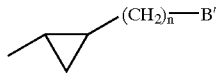   (V)

wherein n is 0 or 1 and B' represents —NHCOR$_a$ or —CONR$_a$, substituted in the 7-position (formula II) by OR$_a$, SR$_a$, or R$_a$, and optionally substituted in the 3-position (formula II) by aryl or arylalkyl, or in the 2-position (formula II) by alkoxy.

14. A compound of claim 1 wherein A represents benzothiophene, benzofuran, indole or azaindole, substituted in the 3-position (formula III) by a group of formula (V):

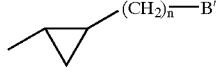   (V)

wherein n is 0 or 1 and B' represents —NHCOR$_a$ or —CONHR$_a$, substituted in the 5-position (formula III) by OR$_a$, SR$_a$, or R$_a$, and optionally substituted in the 2-position (formula III) by aryl or arylalkyl.

15. A compound of claim 1 wherein A represents naphthalene, substituted in the 1-position by a group of formula (V):

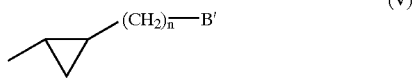   (V)

wherein n is 0 or 1 and B' represents —NHCOR$_a$ or —CONHR$_a$, substituted in the 7-position by OR$_a$, and optionally substituted in the 3-position by aryl or arylalkyl, or in the 2-position by OR$_a$.

16. A compounds of formula (I) according to claim 1 which is selected from the group consisting of:
- ❖N-[2-(7-Methoxy-1-naphthyl)-1-cyclopropyl]acetamide
- ❖N-[2-(7-Methoxy-1-naphthyl)-1-cyclopropyl] propanamide
- ❖N-[2-(7-Methoxy-1-naphthyl)-1-cyclopropyl] butanamide
- ❖N-[2-(7-Methoxy-1-naphthyl)-1-cyclopropyl] cyclopropanecarboxamide
- ❖N-[2-(2,7-dimethoxy-1-naphthyl)-1-cyclopropyl] acetamide
- ❖N-[2-(2,7-dimethoxy-1-naphthyl)-1-cyclopropyl] propanamide
- ❖N-[2-(2,7-dimethoxy-1-naphthyl)-1-cyclopropyl] butanamide
- ❖N-[2-(2-methoxy-1-naphthyl)-1-cyclopropyl]acetamide
- ❖N-[2-(2-methoxy-1-naphthyl)-1-cyclopropyl] propanamide
- ❖N-[2-(2-methoxy-1-naphthyl)-1-cyclopropyl] pbutanamide
- ❖N-[2-(2-methoxy-1-naphthyl)-1-cyclopropylmethyl] acetamide
- ❖N-[2-(2-methoxy-1-naphthyl)-1-cyclopropylmethyl] propanamide
- ❖N-[2-(2-methoxy-1-naphthyl)-1-cyclopropylmethyl] butanamide , its enantiomers and diastereoisomers, and addition salts thereof with a pharmaceutically-acceptable acid or base.

17. A compound of claim 15 wherein the —(CH$_2$)$_n$—B' and R—A—G$_1$-groups are in the trans configuration.

18. A method for treating a living body afflicted with a disorder of the melatoninergic system comprising the step of administering to the living body an amount of a compound of claim 1 which is effective for the alleviation of said condition.

19. A pharmaceutical composition useful for treating melatoninergic disorders comprising, as active principle, an effective amount of a compound as claimed in claime 1, together with one or more pharmaceutically-acceptable excipients or vehicles.

20. A pharmaceutical composition useful for treating melatoninergic disorders comprising as active principle, an effective amount of a compound claimed in claim 16, together with one or more pharmaceutically-acceptable excipients or vehicles.

* * * * *

UNITED STATES PATENT AND TRADEMARK OFFICE
CERTIFICATE OF CORRECTION

PATENT NO. : 6,583,319 B1
DATED : June 24, 2003
INVENTOR(S) : Michel Langlois et al.

It is certified that error appears in the above-identified patent and that said Letters Patent is hereby corrected as shown below:

<u>Title page,</u>
Item [57], ABSTRACT,
Line 1, "for a" should be -- formula --.

<u>Column 24,</u>
Lines 45-50, in the formula "D" should be -- D´ --.

<u>Column 25,</u>
Line 44, "p=q" should be -- p+q --.

<u>Column 27,</u>
Line 32, "-CONR$_a$" should be -- CONHR$_a$ --.

<u>Column 28,</u>
Line 33, correct the spelling of -- butanamide --
Line 50, correct the spelling of -- claim --

Signed and Sealed this

Thirtieth Day of September, 2003

JAMES E. ROGAN
*Director of the United States Patent and Trademark Office*